United States Patent
Sanchez et al.

(10) Patent No.: US 12,254,991 B2
(45) Date of Patent: Mar. 18, 2025

(54) LEARNING CLASSIFIER FOR BRAIN IMAGING MODALITY RECOGNITION

(71) Applicant: Mint Labs Inc., Boston, MA (US)

(72) Inventors: Irina Sanchez, Barcelona (ES); Matthew Rowe, Barcelona (ES); Santiago Puch Giner, Barcelona (ES)

(73) Assignee: Mint Labs, Inc., Duxbury, MA (US)

( * ) Notice: Subject to any disclaimer, the term of this patent is extended or adjusted under 35 U.S.C. 154(b) by 431 days.

(21) Appl. No.: 17/602,547

(22) PCT Filed: Apr. 13, 2020

(86) PCT No.: PCT/US2020/027986
§ 371 (c)(1),
(2) Date: Oct. 8, 2021

(87) PCT Pub. No.: WO2020/210826
PCT Pub. Date: Oct. 15, 2020

(65) Prior Publication Data
US 2022/0189014 A1   Jun. 16, 2022

Related U.S. Application Data

(60) Provisional application No. 62/832,407, filed on Apr. 11, 2019.

(51) Int. Cl.
*G16H 50/70* (2018.01)
*G06T 7/00* (2017.01)
(Continued)

(52) U.S. Cl.
CPC ........... *G16H 50/70* (2018.01); *G06T 7/0012* (2013.01); *G06V 10/764* (2022.01); *G06V 10/77* (2022.01);
(Continued)

(58) Field of Classification Search
CPC ...... G16H 50/70; G06V 10/77; G06V 10/764; G06T 7/0012; G06T 2207/20081; G06T 2207/20084; G06T 2207/30016
See application file for complete search history.

(56) References Cited

U.S. PATENT DOCUMENTS

2017/0032222 A1* 2/2017 Sharma ............... G06V 30/194
2017/0330029 A1 9/2017 Turcot et al.
(Continued)

OTHER PUBLICATIONS

Sahiner et al "Deep Learning in Medical Imaging and Radiation Therapy" The International Journal of Medical Physics Research and Practice (online), pp. e1-e37, published Nov. 20, 2018 (retrieved Jun. 18, 2020). https:// deepblue.lib.umich.edu/bitstream/handle/2027.42/146980/mp13264.pdf?sequence=2.*
(Continued)

*Primary Examiner* — John J Lee
(74) *Attorney, Agent, or Firm* — Foley Hoag LLP; John Lanza; Katherine L. Baker

(57) ABSTRACT

Systems and methods for training a model for identifying an imaging modality. The systems and methods can be performed by a computer system having one or more processors and memory. A plurality of image vectors can be generated from first image data using a convolutional neural network. A loss function can be applied to each of the plurality of image vectors to produce an intermediate dataset. The intermediate dataset can be projected in a space having lower dimensional space that the intermediate dataset. A plurality of clusters can be identified from the intermediate dataset in the space using a clustering technique. Each of the plurality of clusters can be classified into one of a plurality of imaging modalities.

9 Claims, 4 Drawing Sheets

(51) Int. Cl.
 *G06V 10/764* (2022.01)
 *G06V 10/77* (2022.01)
(52) U.S. Cl.
 CPC .............. *G06T 2207/20081* (2013.01); *G06T 2207/20084* (2013.01); *G06T 2207/30016* (2013.01)

(56) References Cited

U.S. PATENT DOCUMENTS

2017/0351936 A1* 12/2017 Jiang ...................... G06V 10/82
2021/0209388 A1* 7/2021 Ciftci ................... G06V 10/764

OTHER PUBLICATIONS

Sahiner et al. "Deep Learning in Medical Imaging and Radiation Therapy." The international Journal of Medical Physics Research and Practice, pp. e1-e37, published Nov. 20, 2018.
International Search Report and Written Opinion for International Application No. PCT/US20/27986 dated Jul. 6, 2020.

* cited by examiner

LEARNING CLASSIFIER FOR BRAIN IMAGING MODALITY RECOGNITION

CROSS-REFERENCE TO RELATED APPLICATIONS

The present application is a National Stage Application, filed under 35 U.S.C. 371, of International Patent Application No. PCT/US2020/027986 filed on Apr. 13, 2020 titled "LEARNING CLASSIFIER FOR BRAIN IMAGING MODALITY RECOGNITION," which in turn claims priority to Application No. 62/832,407, filed Apr. 11, 2019 titled "FEW-SHOT LEARNING VIA TRIPLET NETWORKS FOR BRAIN IMAGING MODALITY RECOGNITION," the entirety of which are incorporated by reference herein.

BACKGROUND

Multiple imaging modalities can be used to identify imaging biomarkers. Each imaging modality is used to assist with specific diagnosis and treatments. Patient's image data may be acquired using different imaging modalities. The image data can be retrieved based on the respective imaging modality to assist with diagnosis and treatment.

SUMMARY

The present disclosure is directed to systems and methods for training a model for identifying an imaging modality using a learning classifier. Useful imaging biomarkers can be identified using multiple imaging modalities, such as computed tomography ("CT"), positron emission tomography ("PET"), single photon emission computed tomography ("SPECT"), magnetic resonance imaging ("MRI"), and other sub-modalities. Each of the imaging modalities can be processed using differently to identify the imaging biomarkers. These imaging biomarkers can assist with different diagnosis, monitoring diseases, and measuring the efficacy of pharmaceutical treatments. The imaging biomarkers can be used in diagnostic workflows and clinical trials to augment the clinical understanding of complex diseases. This diversity of imaging modalities used in modern medicine creates complexity for the image archival systems, such as picture archiving and communication system ("PACS"), and vendor neutral archive ("VNA"), and cloud-based solutions.

Classification of imaging modalities is important for efficient imaging workflows, a particularly difficult problem in MRI, as the many distinct sub-modalities are not differentiated in a simple and consistent manner by header information. Using Convolutional Neural Networks ("CNN"), imaging modalities can be classified and organized, promising to improve the organization of medical image data with automated classification of imaging modalities. However, the use of CNN requires large volumes of annotated data, which can be difficult to obtain for novel imaging biomarkers or rare modalities. In other words, with a scarce amount of available image data, much less annotated data, for novel imaging biomarkers or rare modalities, CNN may not accurately distinguish between different imaging modalities. The present disclosure includes a learning classifier capable of capturing the most relevant imaging features or biomarkers to enable differentiation between imaging modalities using limited amounts of available training examples. The learning classifier can be based on triplet ranking networks.

At least one aspect is directed to a method for training a model for identifying an imaging modality from a limited number of training examples. The method can be performed by a computer system having one or more processors and memory. The method can include generating, from first image data, a plurality of image vectors using a convolutional neural network ("CNN"). The method can include the use of a loss function to guide the learning of an intermediate dataset. The method can include projecting the intermediate dataset in a space having lower dimensional space than the intermediate dataset. The method can include identifying a plurality of clusters from the intermediate dataset in the space using a clustering technique. The method can include classifying each of the plurality of clusters into one of a plurality of imaging modalities.

In some implementations, the method can include generating, from first image data, a plurality of image vectors using a ResNet-50 CNN trained on ImageNet. In some implementations, the method can include storing a plurality of image data in a database, each of the plurality of image data associated with a respective imaging modality. Furthermore, the method can include selecting a first image data of the plurality of image data from the database to generate a plurality of image vectors. In some implementations, the method can include applying a triplet loss function to each of the plurality of image vectors to produce an intermediate dataset. In some implementations, the method can include projecting the intermediate dataset in the space having lower dimensional space than the intermediate dataset using a principal component analysis by performing linear mapping. In some implementations, the method can include projecting the intermediate dataset in the space having lower dimensional space than the intermediate dataset using non-negative matrix factorization by removing negative signals in the dataset.

In some implementations, the method can include selecting, prior to projecting an intermediate dataset in a space, a dimension of the space having lower dimensional space than the intermediate dataset based on a validation performance metric. Furthermore, the method can include projecting, using the dimension selected for the space, the intermediate dataset in the space having lower dimensional space than the intermediate dataset. In some implementations, the method can include identifying the plurality of clusters from the intermediate dataset in the space using at least one of a centroid-based, a density-based, a distribution-based, or a hierarchical clustering technique. In some implementations, the method can include classifying each of the plurality of clusters into one of a plurality of imaging modalities using a cluster-to-class mapping to assign each of the plurality of clusters to a respective imaging modality of the plurality of imaging modalities. In some implementations, the method can include classifying each of the plurality of clusters into one of a plurality of imaging modalities comprising a computed tomography, a positron emission tomography, a single photon emission computed tomography, or a magnetic resonance imaging.

At least one aspect is directed to a system to train a model to identify an imaging modality. The system can include a computer. The computer can include one or more processors and memory. The system can generate, from first image data, a plurality of image vectors using a convolutional neural network ("CNN"). The system can apply a loss function to each of the plurality of image vectors to produce an intermediate dataset. The system can project the intermediate dataset in a space having lower dimensional space than the intermediate dataset. The system can identify a plurality of clusters from the intermediate dataset in the space using a clustering technique. The system can classify each of the plurality of clusters into one of a plurality of imaging modalities.

In some implementations, the system can generate, from first image data, a plurality of image vectors using a ResNet-50 CNN trained on ImageNet. In some implementations, the system can store a plurality of image data in a database, each of the plurality of image data associated with a respective imaging modality. Furthermore, the system can select a first image data of the plurality of image data from the database to generate a plurality of image vectors. In some implementations, the system can apply a triplet loss function to each of the plurality of image vectors to produce an intermediate dataset. In some implementations, the system can project the intermediate dataset in the space having lower dimensional space than the intermediate dataset using a principal component analysis by performing linear mapping. In some implementations, the system can project the intermediate dataset in the space having lower dimensional space than the intermediate dataset using non-negative matrix factorization by removing negative signals in the dataset.

In some implementations, the system can select, prior to projecting an intermediate dataset in a space, a dimension of the space having lower dimensional space than the intermediate dataset based on a validation performance metric. Furthermore, the system can project, using the dimension selected for the space, the intermediate dataset in the space having lower dimensional space than the intermediate dataset. In some implementations, the system can identify the plurality of clusters from the intermediate dataset in the space using at least one of a centroid-based, a density-based, a distribution-based, or a hierarchical clustering technique. In some implementations, the system can classify each of the plurality of clusters into one of a plurality of imaging modalities using a cluster-to-class mapping to assign each of the plurality of clusters to a respective imaging modality of the plurality of imaging modalities. In some implementations, the system can classify each of the plurality of clusters into one of a plurality of imaging modalities comprising a computed tomography, a positron emission tomography, a single photon emission computed tomography, or a magnetic resonance imaging.

These and other aspects and implementations are discussed in detail below. The foregoing information and the following detailed description include illustrative examples of various aspects and implementations, and provide an overview or framework for understanding the nature and character of the claimed aspects and implementations. The drawings provide illustration and a further understanding of the various aspects and implementations, and are incorporated in and constitute a part of this specification.

BRIEF DESCRIPTIONS OF THE DRAWINGS

The accompanying drawings are not intended to be drawn to scale. Like reference numbers and designations in the various drawings indicate like elements. For purposes of clarity, not every component may be labeled in every drawing. In the drawings.

Figure 1:
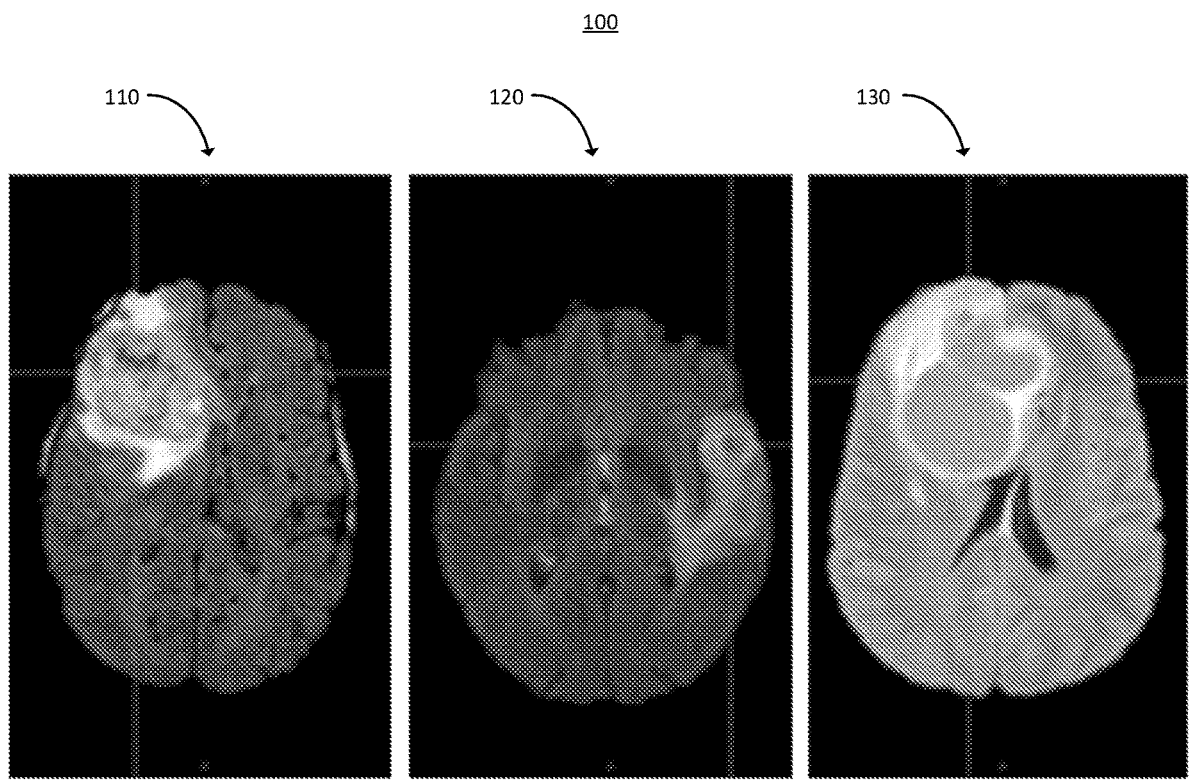
FIG. 1 illustrates axial slices of T2-FLAIR acquisitions of 3 different samples of brain tissue with tumors of variable grade.

FIGS. 4-B illustrates an example projection for training using convolution neural network and a learning classifier.

DETAILED DESCRIPTION

The present solution can capture the most relevant imaging features or biomarkers to enable differentiation between imaging modalities using limited amounts of available training examples. For example, the present solution can use a learning classifier to train a model for identifying an imaging modality corresponding to an image data. The learning classifier can use identify the imaging modality from a limited number of training examples. Using multiple imaging modalities, imaging biomarkers can be identified to assist with different diagnosis, monitoring diseases, and measuring the efficacy of pharmaceutical treatments. The present solution can address the problem of differentiating between imaging modalities given a limited amount of available training examples or image data. In particular, in case of novel imaging biomarkers or rare modalities, training examples corresponding to the imaging biomarkers or the modalities may be scarce or unavailable. Furthermore, these training examples or image data may not be annotated, such as to identify the relevant features or biomarkers associated with the training examples or image data.

Another problem addressed by the present solution is that since the learning classifier can capture the most relevant features or biomarkers using the limited amount of available training examples and image data, this reduces resource consumption and memory allocation. Especially with 3D image data, the present solution can reduce resource consumption and memory allocation requirement, while enabling differentiation between imaging modalities. Each imaging modality can capture at least one relevant feature better than other imaging modalities. The relevant features or biomarkers can include, for example, tumor (e.g., glioma, benign, and malignant), healthy tissues (i.e., normal tissues), infection, clots, or other abnormalities in the brain or other anatomical parts. For example, computer tomography ("CT") scan can capture features related to tumors and cancers, magnetic resonance imaging ("MRI") can capture features related to blood vessels issues and aneurysms, and positron emission tomography ("PET") scan can capture features related to heart diseases and cancers. While relevant features can be captured on different anatomical parts within a human body, the brain can be used as examples for using the learning classifier.

MR imaging can be performed based on magnetization properties of atomic nuclei. The protons are normally oriented in a plurality of directions. An external magnetic field can be introduced to align the protons located within the water nuclei of the brain tissue. For example, the protons are normally oriented to travel in up, down, left, right, or any direction in between. By introducing the external magnetic field, the protons can be oriented to travel in up and down, left and right, front and back, or other directions perpendicular to the introduced magnetic field. The proton alignment can then be disrupted or perturbed by a radio frequency (RF) energy. The disruption can revert the proton alignment to their normally oriented directions. By reverting the proton alignment, RF energy can emit for collection and measurement. The time for reverting the proton alignment can be referred to as relaxation time, which can be utilized to characterize the brain tissue. The measured RF energy can be converted, via Fourier Transformation using the frequency information of the RF energy, to a plurality of intensity levels for generating at least one monochrome MR image. The intensity levels correspond to a lighter or darker portion of the MR image.

FIG. 1 illustrates an example axial slices 100 of T2-FLAIR acquisitions of 3 different samples of brain tissue with tumors (e.g. glioma) of variable grade. The axial slices 100 present a 2D top-down perspective of the brains. The axial slices 100 can include a first image 110, a second image 120, and a third image 130, each representing a different brain with tumor. The tumor location, extension, and shape can be highly heterogeneous. The distinction between the first image 110, the second image 120, and the third image 130, can demonstrate uses of different imaging modalities. Each of the imaging modalities can capture one or more features (e.g., tumor) better than the other.

Depending on the size, shape, and location of each glioma, one imaging modality can capture relevant features better than others. The imaging modality can include a computed tomography ("CT"), a positron emission tomography ("PET"), a single photon emission computed tomography ("SPECT"), or a magnetic resonance imaging ("MRI"), for example. Additionally, if the image data includes novel imaging biomarkers or rare modalities, where limited amounts of training examples are available, relevant features may not be captured to accurately identify the imaging modality used to obtain the image data. By using the learning classifier, the most relevant features can be captured to differentiate between imaging modalities for efficient imaging workflow by reducing processing time or image data retrieval. The retrieval time is reduced as retrieval information (e.g., formats of the image data) are provided to facilitate data retrieval.

Figure 2:
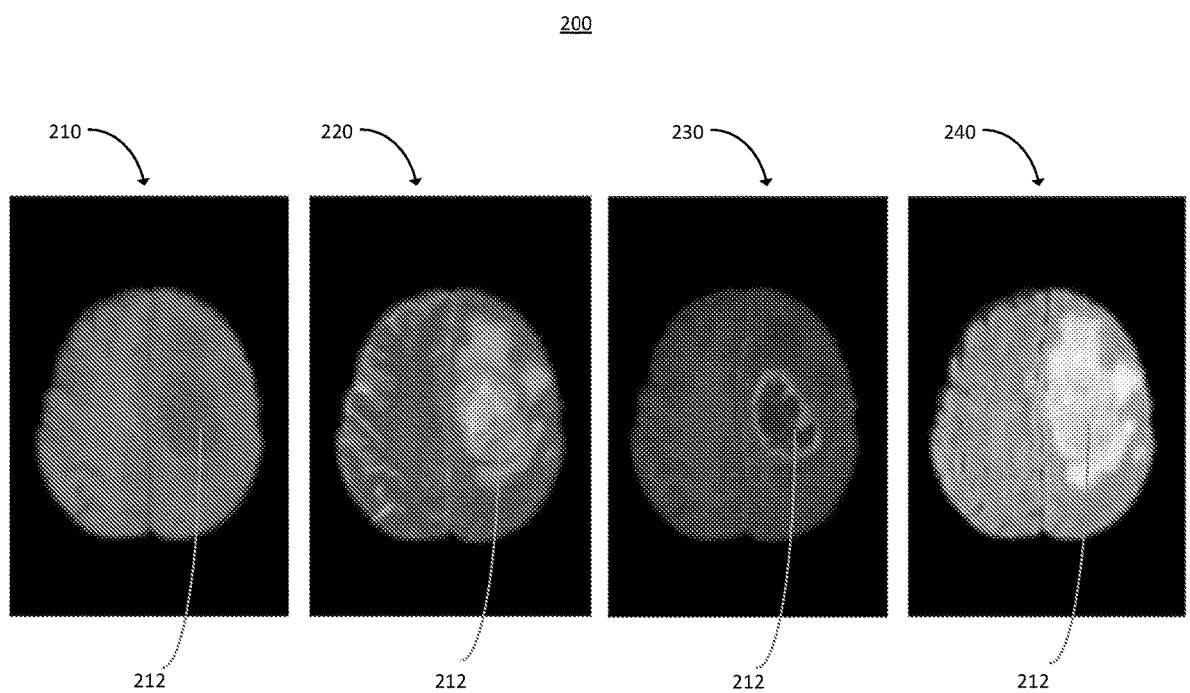
FIG. 2 illustrates axial slices of T1-weighted acquisitions, T2-weighted acquisitions, T1 Gadolinium enhanced acquisitions, and T2-FLAIR acquisitions of brain tissue.

FIG. 2 illustrates an example axial slices 200 of T1-weighted acquisitions, T2-weighted acquisitions, T1 Gadolinium enhanced acquisitions, and T2-FLAIR acquisitions of brain tissue. The various acquisitions of brain tissue can refer to at least one of imaging modalities, such as MRI, PET, CT, or SPECT. For this illustrated example, MR modality (i.e., MRI modality) may be used to obtain the axial slices 200. The axial slices 200 present a 2D top-down perspective, similar to FIG. 1. The axial slices 200 includes a first image 210, a second image 220, a third image 230, and a fourth image 240, all of which are the same brain using various MR modalities. The axial slices 200 further includes the same glioma 212 in the MR images. The MR modalities can include T1-weighted, T2-weighted, FLAIR, and contrast enhanced T1 (Gadolinium contrast), abbreviated as T1-Gd. The MR modalities can refer to, and use interchangeably with other descriptive terms, such as protocols, modes, and methods of MR imaging. The MR modalities can each emphasize different healthy and abnormal tissues, such as to highlight or conceal one or more portions of the brain. For example, the T1-Gd modality can include Gadolinium contrast injected intravenously and at the administered concentrations to initiate an effect of reducing T1 relaxation time, which increases T1 signal.

The MR modalities can be differentiated by Repetition Time (TR) and Time to Echo (TE). The TR represents a time between successive pulse sequences that are applied to the same axial slice 200. The time between successive pulse sequences can be, for example, 200 millisecond (ms), 3330 ms, or 4505 ms. The TE represents a time between delivery of the RF pulse and the receipt of the echo signal. The mentioned TE time can be, for example, 13 ms, 55 ms, or 94 ms. Each MR modality can be based on different relaxation times. The relaxation times referring to the duration for the aligned protons to revert back to a resting or normal orientation. The resting or normal orientations can refer to the orientations of the protons prior to applying the external magnetic field, such that the protons resume to travel in random directions.

T1 can refer to a longitudinal relaxation time. T1 represents a time constant to determine a rate for excited protons to return to equilibrium. The protons can be excited by, for example, applying a magnetic field to align and orient the protons in a direction and an opposite direction. In further definition, T1 is a time measurement for spinning protons to realign with the external magnetic field. T2 can refer to a traverse relaxation time. T2 represents a time constant to determine the rate for the excited protons to reach equilibrium or depart from the phases of other protons. The time constant of T2 measures a time for spinning protons to lose phase coherence from the nuclei spinning perpendicularly to the applied magnetic field.

The first image 210 includes the glioma 212 situated in the right hemispheric parietal lobe of the brain. The first image 210 uses T1-weighted protocol to enhance the MR image. T1-weighted protocol can be based on T1-relaxation properties. The T1-relaxation properties can refer to the time measurement for the spinning protons to realign with the external magnetic field, as described previously. With the T1-relaxation properties, T1-weighted protocol can approximate the anatomy of an organ of interest. T1-weighted protocol can generate the first image 210 with various intensities based on different types of matter. For example, the first image 210, using T1-weighted protocol, can display fluids, such as CSF, with low intensity value, such as 5 lux (lx), 13 lx, or 18 lx. The fluids, as in the first image 210, can feature the glioma 212. The first image 210 can further display white matter with high intensity value, such as 100 lx, 120 lx, or 133 lx, and display gray matter with intermediate intensity value, such as 50 lx, 66 lx, or 70 lx. The intermediate intensity can refer to an intensity value greater than the low intensity value, but less than the high intensity value. As an example, the first image 210 displays the glioma 212 with low intensity value, and different portions of the brain with intermediate and high intensity value. However, the low intensity value, as in the example, is subtle relative to the different portions of the brain, such that the glioma 212 may not be easily distinguished from the healthy portions of the brain (e.g. the different portions with intermediate and/or high intensity values).

The second image 220 includes the same glioma 212 as the first image 210. The second image 220 uses T2-weighted protocol to enhance the MR image. T2-weighted protocol can be based on T2-relaxation properties. The T2-relaxation properties can refer to the time measurement for the spinning protons to lose phase coherence from the nuclei spinning perpendicularly to the applied magnetic field. T2-weighted protocol, given the T2-relaxation properties, can display the second image 220 with inverse intensity value to the first image 210. For example, the second image 220 can exhibit the fluids (e.g. the glioma 212 or edema, which refers to abnormal accumulation of fluids in certain tissue of the brain) as high intensity value, the gray matter as intermediate intensity value, and the white matter as low intensity value. As demonstrated in the second image 220, the glioma 212 appears with higher intensity than the healthy portions of the brain, such that the healthy portions of the brain appear with low intensity value enclosing the glioma 212.

The third image 230 includes the same glioma 212 as the first image 210 and the second image 220. The third image 230 uses T1-Gd protocol to enhance the MR image. T1-Gd protocol can include Gadolinium (Gad), which is a non-toxic paramagnetic contrast enhancement agent. The Gad can be used to shorten the longitudinal relaxation time (e.g. T1) for configuring the signal intensities. The Gad can be injected intravenously and at a medically appropriate concentration, such as to reduce T1 relaxation time for an increase in T1 signal. The increased T1 signal can cause the Gad to appear very bright. For example, T1-Gd protocol can induce perimeters of the glioma 212 of the third image 230 to appear brighter than the healthy tissue and the central portions of the glioma 212. The perimeters can refer to the contour of the glioma 212. By highlighting the contour of the glioma 212, the glioma 212 can distinguish from the healthy brain tissue in the third image 230 of the axial slices 200. T1-Gd protocol can highlight vascular structures and breakdowns in the blood-brain barrier [e.g. tumor, abscesses, inflammation (herpes simplex encephalitis, multiple sclerosis, etc.)].

Although the illustrated example can include MR modality to acquire the axial slices 200, as in FIG. 2, if training examples are scarce or information regarding the imaging modality of the image data is unavailable, the imaging modality may not be accurately identified. However, using the learning classifier, one or more relevant features of the image data can be captured, enabling differentiation between imaging modalities. Referring still to FIG. 2, and as an example, once the image data are classified with an imaging modality, efficiency of imaging workflow (e.g., retrieval of the image data) can improve as the system can use a format corresponding to the imaging modality to retrieve the image data. In addition to reducing image data retrieval time, using the learning classifier can avoid inaccurate classification of imaging modality on image data with limited training examples. By classifying the image data with a false imaging modality, the time to retrieve image data may be prolonged.

Figure 3:
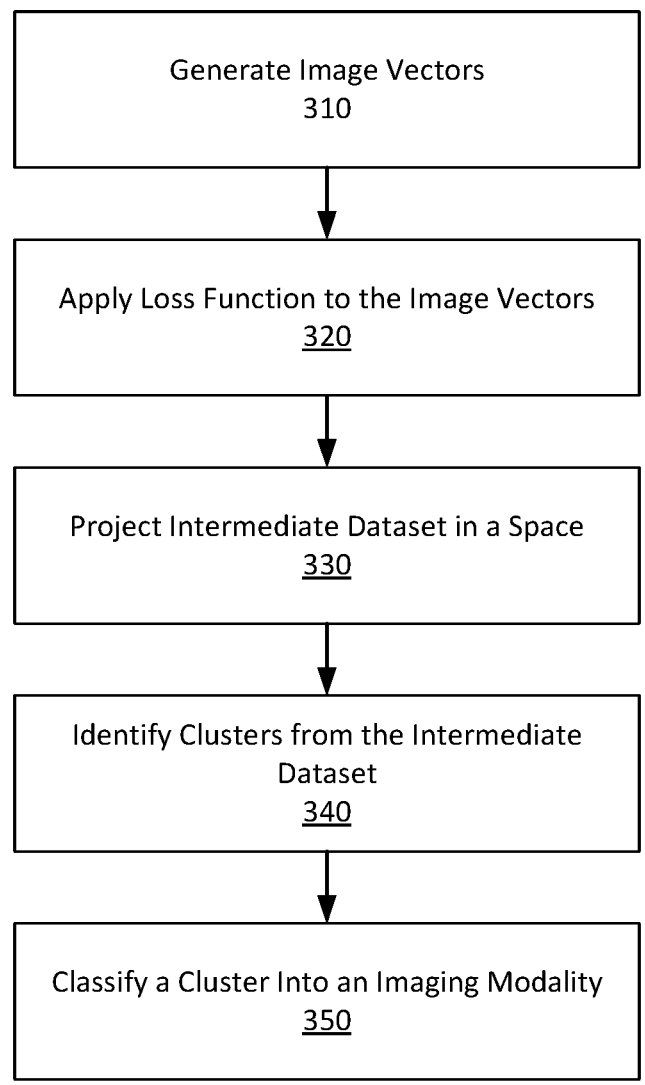
FIG. 3 illustrates an example flow diagram of a method for training a model for identifying imaging modality.

Referring generally to FIG. 3, a flow diagram depicting an example method 300 for training a model for identifying imaging modality is depicted. The method 300 can be performed by a computer system having one or more processors and memory. In brief overview, at step 310, the computer system can generate a plurality of image vectors using a convolutional neural network from first image data. At step 320, the computer system can apply a loss function to each of the plurality of image vectors to produce an intermediate dataset. At step 330, the computer system can project the intermediate dataset in a space having lower dimensional space than the intermediate dataset. At step 340, the computer system can identify a plurality of clusters from the intermediate dataset in the space using a clustering technique. At step 350, the computer system can classify each of the plurality of clusters into one of a plurality of imaging modalities.

Still referring to FIG. 3, at step 310 and in further details, the computer system can generate a plurality of image vectors using a convolutional neural network from first image data. The imaging vectors can be referred to as, and use interchangeably with other descriptive terms, such as imaging embedding and embedding vectors. The imaging vectors can be used to produce an intermediate dataset for classification of imaging modality. The imaging modality may be referred to generally as modality. The imaging vectors can be the outputs of the convolutional neural network.

In some implementations, the image data can be retrieved from a database. The database can be a centralized storage, internal storage, external storage, or cloud-based storage. Each image data can correspond to their respective imaging modality. For example, first image data may be acquired using MRI and second image data may be acquired using PET scan. The image data may be selected from the database for classification of their imaging modality. In some cases, the computer system may access all image data stored in the database to automatically classify each image data with their respective imaging modality. The one or more selected image data can be used to generate the image vectors.

The generation of the imaging vectors can provide a reduction of dimensionality of the input data. The reduction of the dimensionality can refer to reducing the size of the image data to be processed for classification. For example, with 20-megapixel photograph with three RGB layers, over 60 million integers would be processed. By generating the imaging vectors from the photograph or picture using the convolutional neural network, the 60 million integers may be reduced to half the dimensions or less, for example. The reduction of the dimensionality can focus on the most relevant features for classification of imaging modalities, such that features not relevant to the classification of imaging modality may not be processed. In some cases, the imaging vectors can be triplets to reduce the dimensionality of the input volume or image data.

Convolutional neural network ("CNN") architecture can refer to a machine learning or artificial intelligence ("AI") architecture. CNN can generate the imaging vectors as the output from processing the image data or imaging data. CNN architecture can include various layers, such as dimensions adaptation layer, initialize convolution, residual layer, downsample layer. CNN architecture can receive or retrieve an input volume including one or more 2D slices of data from, for example, the data ingestion pipeline, the database, or a cloud via a network. In some implementations, 3D volumes may be stored in the database, used to generate the 2D slices for processing by CNN architecture. The input slice can include predetermined dimensions, such as the length, and height. The input slice can refer to an image data to generate multiple imaging vectors. These image data can be associated with an imaging modality, such as using MRI, CT scan, PET scan, or X-ray to acquire the image data.

In some implementations, the computer system can employ a ResNet-50 CNN trained on ImageNet to process the input volume or image data. The ResNet-50 can reduce the dimensionality of the image data for capturing the relevant features and removing the irrelevant features. Subsequent to reducing the dimensionality of the image data, the ResNet-50 can transfer the knowledge of this task (i.e., the output imaging vectors) to a database for fine-tuning. The fine-tuning of the database can refer to improving various image data stored in the database, such as by way of annotation or reduction of dimensionality for the stored image data. In some other implementations, other CNN architecture can be employed to reduce the dimensionality of the image data, such as LeNet, AlexNet, ZFNet, GoogLeNet, or VGGNet.

At step 320, and in further details, the computer system can apply a loss function to each of the plurality of image vectors to produce an intermediate dataset. The loss function can include a triplet loss function, regression loss function, binary classification loss function, or multi-class classification loss function, for example. The loss function can be used to produce an intermediate dataset to be processed by the computer system. In particular, the loss function can be applied to the imaging vectors to evaluate how well each imaging vector fits in with the intermediate dataset. For example, if one or more imaging vectors does not contribute to identifying the relevant feature of the image data, the loss function can output a high rating (e.g., 5 out of 5). Instead, if the one or more imaging vectors contributes to the relevant features, the loss function can output a lower rating (e.g., 1 out of 5 or 2 out of 5).

In further example, the loss function can reduce the imaging vectors based on a threshold, such as 4 out of 5 rating. In this case, the loss function can remove any imaging vector above the indicated threshold. The threshold may be predetermined or automatically configured based on the results of differentiating the imaging modalities. Once the loss function removes or filters the imaging vectors, an intermediate dataset can be produced for projection. The intermediate dataset can refer to a set of data for projecting into a space to identify one or more clusters for classification or differentiation of imaging modality.

In some implementations, the computer system can use the loss function to enforce instances from the same class (e.g., imaging modalities) to be close in the embedding space under the L1 metric. L1 metric can be referred to as an L1 norm, which is the sum of absolute pixel value. The loss function can enforce instances from different classes to be projected further away. The system can incorporate additional elements in the definition of the loss to guide training and create a more representative embedding space for the task. The additional elements can include processed data from other image data. For example, the system can penalize the L2 norm of the imaging vectors, and the system can mine hard examples for each batch (online hard-mining). This can result in taking into account only the greatest distance between two instances of the same class and the smallest distance between two instances of different classes. Taking into account can refer to including the instances or removing other instances not being accounted for. Only Hard examples can refer to training examples or dataset with borderline cases (e.g., image data where live human face and painting of a human face is not as distinguishable) to train the learning classifier model.

At step 330, and in further details, the computer system can project the intermediate dataset in a space having lower dimensional space than the intermediate dataset. At step 340, the computer system can identify a plurality of clusters from the intermediate dataset in the space using a clustering technique. The space can be referred to as, and use interchangeably with other descriptive terms, such as an embedding space or dimensionality. The projection of the intermediate dataset in the space can refer to filtering or focusing the intermediate dataset to an area or region more relevant for classification of the image data features. Lowering the dimensional space of the intermediate dataset can reduce or remove noise components of the dataset, such that the computer system does not falsely classify the noise as the relevant feature of the image data.

In some implementations, the intermediate dataset can be projected in lower dimensional space using principal component analysis ("PCA"). The PCA function can reduce dimensionality of dataset to retain most relevant or variation in the dataset. The PCA can reduce the dimensionality of the intermediate dataset by performing linear mapping. In some implementations, the intermediate dataset can be projected in lower dimensional space using non-negative matrix factorization ("NMF"). Similar to the PCA, the NMF can reduce the dimensionality of the dataset to retain features relevant for classification of imaging modalities. The NMF reduces the dimensionality by removing negative signals in the dataset.

In some implementations, prior to projecting the intermediate dataset in the lower dimensional space, the dimension of the lower dimensional space can be selected based on a validation performance metric. The validation performance metric can quantify the quality of various dimensional space for acquiring the most relevant features, such as to accurately classify the imaging modality. In some cases, highest quantified dimensional space can be selected based on the image data selected for classification of imaging modality. Subsequent to selecting a dimensional space, the intermediate data can be projected to the selected dimensional space to identify the most relevant features.

At step 340, and in further details, the computer system can identify a plurality of clusters from the intermediate dataset in the space using a clustering technique. The clustering technique can include at least a centroid-based, a density-based, a distribution-based, or a hierarchical clustering technique. For example, the distribution-based clustering technique can include Gaussian Mixture Model ("GMM") for clustering the intermediate dataset to provide soft-assignments using posterior probability. The computer system can use the clustering technique to group portions of the intermediate dataset that include features most relevant to the classification of imaging modality.

At step 350, and in further details, the computer system can classify each of the plurality of clusters into one of a plurality of imaging modalities. The classification can be performed by using a cluster-to-class mapping (or cluster-to-label mapping) by assigning each cluster of the intermediate dataset to a respective class. The class can refer to a label depicting a respective feature grouped by the clustering technique. The label can refer to different modalities, such as CT, FDG-PET, T2, T1, T2-Flair, T1-post, PD, MRA and PASL. Subsequent to classifying each cluster into their respective class, such as to group the most relevant features acquired from image data, the computer system can classify the imaging modality pertained to the image data used to generate the imaging vectors.

Figure 4A:
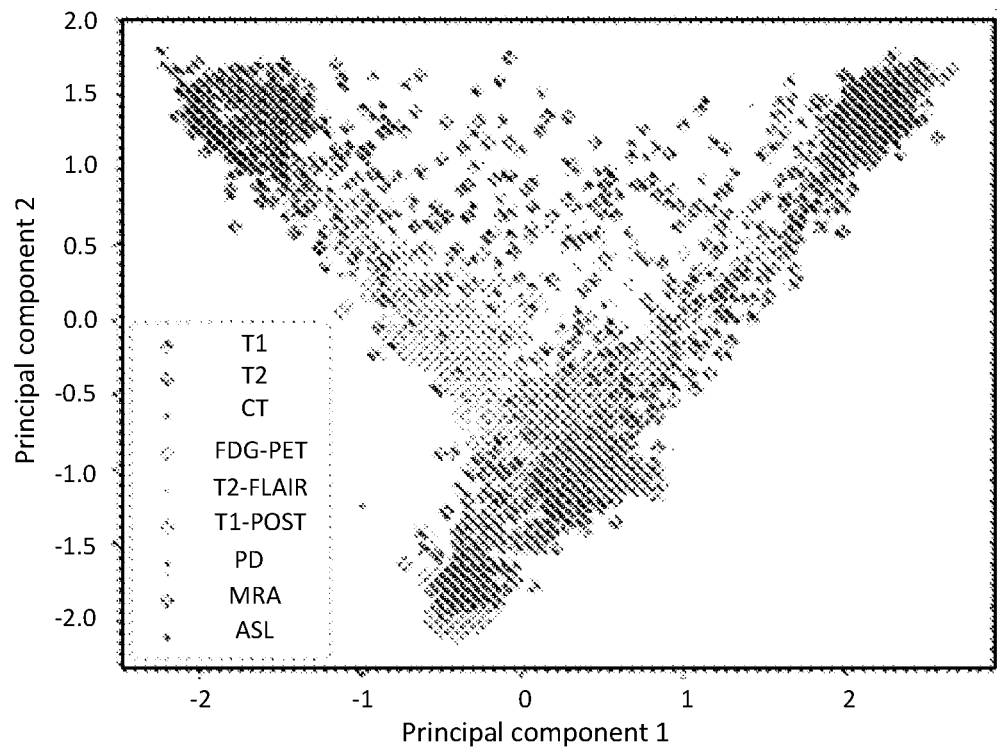
Figure 4B:
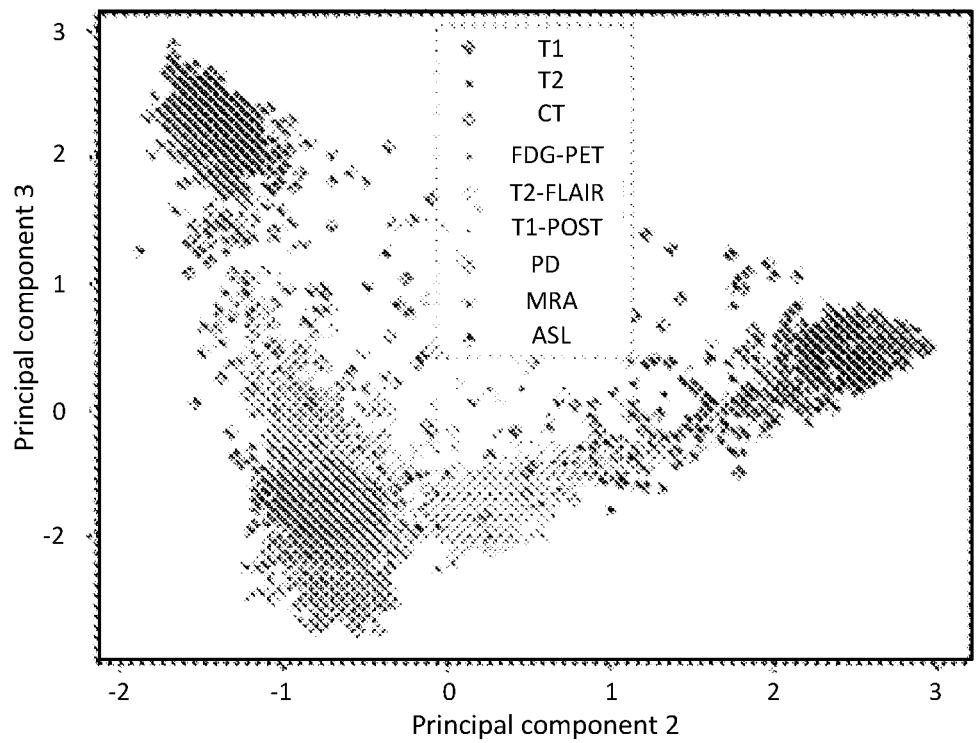

Referring to generally to FIGS. 4A-B, an illustrate depicting an example projection 400 for training using convolution neural network and a learning classifier is shown. FIG. 4A depicts a projection evaluating the performance when training with all available data. FIG. 4B depicts a projection evaluating the performance of the learning classifier training with limited instances or training examples. The depicted projections of FIGS. 4A-B can include T1, post-contrast T1, T2-FLAIR, PD, ASL, MRA, CT and fluorodeoxyglucose ("FDG")-PET data plot. The data plot are clustered over the principal components as the axes.

In some implementations, an imaging database (e.g., brain imaging database) can be used to evaluate the effectiveness of the learning classifier process. Dataset stored in the database can include 7 MRI sequences (e.g., T1, T2, post-contrast T1, T2-FLAIR, PD, ASL and MRA), CT and FDG-PET imaging. These datasets can be sourced from centralized databases or cloud-based storages including brain scans from healthy and diseased individuals.

In some implementations, to train and evaluate the models, the system can extract 2D slices by sampling a normal distribution centered around the middle slice of the brain along the sagittal, coronal and axial axes. The system can extract 30874 slices for T1, 231759 for T2, 18541 for CT, 15432 for FDG-PET, 8017 for post-contrast T1, 8017 for T2-FLAIR, 8370 for PD, 5321 for ASL and 8462 for MRA.

Multiple experiments were conducted using the learning classifier. The experiments were conducted to determine the accuracy of the computer system using limited training examples and dataset. Two of those experiments were: 1) training with all the available data; and 2) train with restrictions on the number of slices of the classes (post-contrast T1, T2-FLAIR, PD, MRA and ASL). Specifically, the learning classifier were trained with restriction to only 150 slices, which corresponds to 10 volumes from which 5 slices have been sampled per direction. In both experiments, the system can compare the performance of the learning classifier against a standard CNN classifier based on the same pre-trained weights and the same architecture plus a fully-connected layer to directly predict the imaging modality from the imaging data. In some cases, the class can refer to imaging modalities or labels depicting the image data.

The results for the two experiments can be shown below in Table 1, when using the learning classifier (Triplet) and the standard CNN classifier (Baseline). The macro-average for the base classes (b) and the triplet classes (f) are computed.

TABLE 1

| Model | Precision (b) | Recall (b) | F1-score (b) | Precision (f) | Recall (f) | F1-Score (f) | Accuracy |
|---|---|---|---|---|---|---|---|
| Baseline - exp 2 | 0.80 | 0.92 | 0.84 | 0.97 | 0.41 | 0.52 | 0.64 |
| Triplet - exp 2 | 0.99 | 0.93 | 0.96 | 0.86 | 0.99 | 0.92 | 0.97 |

The system can train the networks with a batch size of 64, ADAM optimizer, L2 regularization of weights of $1e^{-5}$ and learning rate $5e^{-5}$, for a maximum of 100 epochs with early stopping based on loss. The system can set the margin of the triplet loss to 2, the L2 penalization of the embedding to 0.05, and the dimension of the embedding space to 64.

Table 1 shows the results of the experiments. While the CNN classifier can classify the classes when trained with all the available data, it is unable to capture the relevant imaging traits of the triplet classes when the training data is scarce. However, the learning classifier is able to produce an embedding space that separates imaging modalities into distinct clusters. This results in a classification performance over 0.9 in both experimental settings. Additionally, the data illustrates an increase in performance on the triplet network trained with limited data against the same network trained with all the available data. This can be attributed to local optima, instability of the loss function, premature early stopping, or other factors contributed to managing all available data. Therefore, the use of learning classifier, in addition to enabling differentiation of imaging modalities between image data, is able to outperform the standard CNN classifier in terms of capturing the relevant imaging traits of the triplet classes when all data are available.

The systems and methods described above can provide multiple ones of any or each of those components and these components can be provided on either a standalone system or on multiple instantiation in a distributed system. In addition, the systems and methods described above can be provided as one or more computer-readable programs or executable instructions embodied on or in one or more articles of manufacture. The article of manufacture can be cloud storage, a hard disk, a CD-ROM, a flash memory card, a PROM, a RAM, a ROM, or a magnetic tape. In general, the computer-readable programs can be implemented in any programming language, such as LISP, PERL, C, C++, C#, PROLOG, or in any byte code language such as JAVA. The software programs or executable instructions can be stored on or in one or more articles of manufacture as object code.

Example and non-limiting module implementation elements include sensors providing any value determined herein, sensors providing any value that is a precursor to a value determined herein, datalink or network hardware including communication chips, oscillating crystals, communication links, cables, twisted pair wiring, coaxial wiring, shielded wiring, transmitters, receivers, or transceivers, logic circuits, hard-wired logic circuits, reconfigurable logic circuits in a particular non-transient state configured according to the module specification, any actuator including at least an electrical, hydraulic, or pneumatic actuator, a solenoid, an op-amp, analog control elements (springs, filters, integrators, adders, dividers, gain elements), or digital control elements.

The subject matter and the operations described in this specification can be implemented in digital electronic circuitry, or in computer software, firmware, or hardware, including the structures disclosed in this specification and their structural equivalents, or in combinations of one or more of them. The subject matter described in this specification can be implemented as one or more computer programs, e.g., one or more circuits of computer program instructions, encoded on one or more computer storage media for execution by, or to control the operation of, data processing apparatuses. Alternatively, or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. While a computer storage medium is not a propagated signal, a computer storage medium can be a source or destination of computer program instructions encoded in an artificially generated propagated signal. The computer storage medium can also be, or be included in, one or more separate components or media (e.g., multiple CDs, disks, or other storage devices include cloud storage). The operations described in this specification can be implemented as operations performed by a data processing apparatus on data stored on one or more computer-readable storage devices or received from other sources.

The terms "computing device", "component" or "data processing apparatus" or the like encompass various apparatuses, devices, and machines for processing data, including by way of example a programmable processor, a computer, a system on a chip, or multiple ones, or combinations of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, app, script, or code) can be written in any form of programming language, including compiled or interpreted languages, declarative or procedural languages, and can be deployed in any form, including as a stand-alone program or as a module, component, subroutine, object, or other unit suitable for use in a computing environment. A computer program can correspond to a file in a file system. A computer program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatuses can also be implemented as, special purpose logic circuitry, e.g., an FPGA (field programmable gate array) or an ASIC (application specific integrated circuit). Devices suitable for storing computer program instructions and data can include non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

The subject matter described herein can be implemented in a computing system that includes a back end component, e.g., as a data server, or that includes a middleware component, e.g., an application server, or that includes a front end component, e.g., a client computer having a graphical user interface or a web browser through which a user can interact with an implementation of the subject matter described in this specification, or a combination of one or more such back end, middleware, or front end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

While operations are depicted in the drawings in a particular order, such operations are not required to be performed in the particular order shown or in sequential order, and all illustrated operations are not required to be performed. Actions described herein can be performed in a different order.

Having now described some illustrative implementations, it is apparent that the foregoing is illustrative and not limiting, having been presented by way of example. In particular, although many of the examples presented herein involve specific combinations of method acts or system elements, those acts and those elements may be combined in other ways to accomplish the same objectives. Acts, elements and features discussed in connection with one implementation are not intended to be excluded from a similar role in other implementations or implementations.

The phraseology and terminology used herein is for the purpose of description and should not be regarded as limiting. The use of "including" "comprising" "having" "containing" "involving" "characterized by" "characterized in that" and variations thereof herein, is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

Any references to implementations or elements or acts of the systems and methods herein referred to in the singular may also embrace implementations including a plurality of these elements, and any references in plural to any implementation or element or act herein may also embrace implementations including only a single element. References in the singular or plural form are not intended to limit the presently disclosed systems or methods, their components, acts, or elements to single or plural configurations. References to any act or element being based on any information, act or element may include implementations where the act or element is based at least in part on any information, act, or element.

Any implementation disclosed herein may be combined with any other implementation or embodiment, and references to "an implementation," "some implementations," "one implementation" or the like are not necessarily mutually exclusive and are intended to indicate that a particular feature, structure, or characteristic described in connection with the implementation may be included in at least one implementation or embodiment. Such terms as used herein are not necessarily all referring to the same implementation. Any implementation may be combined with any other implementation, inclusively or exclusively, in any manner consistent with the aspects and implementations disclosed herein.

References to "or" may be construed as inclusive so that any terms described using "or" may indicate any of a single, more than one, and all of the described terms. For example, a reference to "at least one of 'A' and 'B'" can include only 'A', only 'B', as well as both 'A' and 'B'. Such references used in conjunction with "comprising" or other open terminology can include additional items.

Where technical features in the drawings, detailed description or any claim are followed by reference signs, the reference signs have been included to increase the intelligibility of the drawings, detailed description, and claims. Accordingly, neither the reference signs nor their absence have any limiting effect on the scope of any claim elements.

Modifications of described elements and acts such as variations in sizes, dimensions, structures, shapes and proportions of the various elements, values of parameters, mounting arrangements, use of materials, colors, orientations can occur without materially departing from the teachings and advantages of the subject matter disclosed herein. For example, elements shown as integrally formed can be constructed of multiple parts or elements, the position of elements can be reversed or otherwise varied, and the nature or number of discrete elements or positions can be altered or varied. Other substitutions, modifications, changes and omissions can also be made in the design, operating conditions and arrangement of the disclosed elements and operations without departing from the scope of the present disclosure.

The systems and methods described herein may be embodied in other specific forms without departing from the characteristics thereof. Scope of the systems and methods described herein is thus indicated by the appended claims, rather than the foregoing description, and changes that come within the meaning and range of equivalency of the claims are embraced therein.

What is claimed is:

1. A method for training a model for identifying an imaging modality from a limited number of training examples, comprising:
    generating, from first image data, a plurality of image vectors using a convolutional neural network;
    applying a loss function to each of the plurality of image vectors to produce an intermediate dataset;
    projecting the intermediate dataset in a space having lower dimensional space than the intermediate dataset;
    identifying a plurality of clusters from the intermediate dataset in the space using a clustering technique; and
    classifying each of the plurality of clusters into one of a plurality of imaging modalities.

2. The method of claim 1, wherein the step of generating the plurality of image vectors comprises generating, from the first image data, the plurality of image vectors using a ResNet-50 convolutional neural network trained on ImageNet.

3. The method of claim 1, further comprising:
    storing a plurality of image data in a database, each of the plurality of image data associated with a respective imaging modality; and
    selecting the first image data of the plurality of image data from the database.

4. The method of claim 1, wherein the step of applying the loss function comprises applying a triplet loss function to each of the plurality of image vectors to produce the intermediate dataset.

5. The method of claim 1, wherein the step of projecting the intermediate dataset in the space comprises projecting the intermediate dataset in the space having lower dimensional space than the intermediate dataset using a principal component analysis by performing linear mapping.

6. The method of claim 1, wherein the step of projecting the intermediate dataset in the space comprises projecting the intermediate dataset in the space having lower dimensional space than the intermediate dataset using non-negative matrix factorization by removing negative signals in the intermediate dataset.

7. The method of claim 1, further comprising:
    Selecting, prior to projecting the intermediate dataset in the space, a dimension of the space having lower dimensional space than the intermediate dataset based on a validation performance metric; and
    Projecting, using the dimension selected for the space, the intermediate dataset in the space having lower dimensional space than the intermediate dataset.

8. The method of claim 1, wherein the step of identifying the plurality of clusters comprises identifying the plurality of clusters from the intermediate dataset in the space using at least one of a centroid-based, a density-based, a distribution-based, or a hierarchical clustering technique.

9. The method of claim 1, wherein the step of classifying each of the plurality of clusters comprises classifying each of the plurality of clusters into one of the plurality of imaging modalities using a cluster-to-class mapping to assign each of the plurality of clusters to a respective class.

* * * * *